United States Patent
DiFoggio et al.

(10) Patent No.: US 6,714,872 B2
(45) Date of Patent: Mar. 30, 2004

(54) METHOD AND APPARATUS FOR QUANTIFYING PROGRESS OF SAMPLE CLEAN UP WITH CURVE FITTING

(75) Inventors: Rocco DiFoggio, Houston, TX (US); Jaedong Lee, Houston, TX (US)

(73) Assignee: Baker Hughes Incorporated, Houston, TX (US)

(*) Notice: Subject to any disclaimer, the term of this patent is extended or adjusted under 35 U.S.C. 154(b) by 0 days.

(21) Appl. No.: 10/229,228

(22) Filed: Aug. 27, 2002

(65) Prior Publication Data
US 2003/0163259 A1 Aug. 28, 2003

Related U.S. Application Data
(60) Provisional application No. 60/359,895, filed on Feb. 27, 2002.

(51) Int. Cl.$^7$ .................................................. G01V 8/00
(52) U.S. Cl. ......................................................... 702/12
(58) Field of Search ................................. 702/6, 11, 12, 702/13; 73/152, 19, 152.24, 152.28, 152.55; 250/269.1

(56) References Cited

U.S. PATENT DOCUMENTS

| 6,274,865 B1 | | 8/2001 | Schroer et al. |
| 6,343,507 B1 | * | 2/2002 | Felling et al. ............ 73/152.19 |
| 6,350,986 B1 | * | 2/2002 | Mullins et al. ........... 250/269.1 |

OTHER PUBLICATIONS

Hammond, One– and Two–Phase Flow During Fluid Sampling by a Wireline Tool, 1991, pp. 299–330.

Hashem et al., SPE 39093: Determination of Producible Hydrocarbon Type and Oil Quality in Wells Drilled with Synthetic Oil–Based Muds, Oct. 1997, pp. 353–366.

\* cited by examiner

Primary Examiner—Donald E. McElheny, Jr.
(74) Attorney, Agent, or Firm—Madan, Mossman & Sriram, P.C.

(57) ABSTRACT

The present invention provides method of quantifying sample clean up in real time by providing curve-fitting measurements of optical or physical properties of fluid samples in boreholes. Sample fluid is extracted from the formation surrounding the borehole. As fluid continues to be extracted the composition of the extracted sample changes, altering the values of physical properties of the sample being measured. Measurements are made of optical or physical properties of the sampled fluid, and regression analysis is performed on the acquired measured data points. In one embodiment of the invention, iterative methods enable a user to determine an asymptotic value of a physical property, i.e. absorbance, as well as the percent of the progress that the current sample has obtained toward reaching the asymptotic property value and a projected time to reach the asymptotic property value. If the projected time required to reach that asymptotic value is too long, the operator may decide to abandon extracting fluid from the region. In another embodiment, a more general method enables the user to estimate, through the value of a variable, the speed at which cleanup can occur. The physical properties of the sample may be fit as a function of pumping time or volume.

28 Claims, 10 Drawing Sheets

FIG. 1

P value is 1.1 when the invasion is 15 cm

FIG. 2

P value decreases to −.092 as the invasion gets deeper (25 cm)

Curve fit to field data showing P value of 0.637 after 8000 seconds of pumping, and the estimated contamination is 23%.

METHOD AND APPARATUS FOR QUANTIFYING PROGRESS OF SAMPLE CLEAN UP WITH CURVE FITTING

CROSS REFERENCED TO RELATED APPLICATIONS

This application is related to and claims priority from U.S. Patent Application No. 60/359,895, entitled "A Method and Apparatus for Quantifying Progress of Sample Clean Up with Curve Fittings" by Rocco DiFoggio and Jaedong Lee, filed on Feb. 27, 2002.

COPYRIGHT NOTICE

A portion of the disclosure of this patent document contains material to which the claim of copyright protection is made. The copyright owner has no objection to the facsimile reproduction by any person of the patent document or the patent disclosure, as it appears in the U.S. Patent and Trademark Office file or records, but reserves all other rights whatsoever.

Field of the Invention

The invention relates generally to a method for quantifying sample cleanup in real time in a wellbore environment. Specifically, the invention is a method of curve-fitting measurements of physical properties measured for fluid samples being pumped from a formation surrounding a wellbore by a wireline or monitoring while drilling formation tester to predict the time at which a sample having a desired purity can be obtained.

Background of the Invention

In wellbore exploration, typically drilling muds such as oil-based muds and synthetic-based muds or water-based muds are used. The filtrates from these muds generally invade the formation through the borehole wall to an extent, meaning that this filtrate must be removed from the formation in order to access the formation fluids. Open hole sampling is an effective way to acquire representative reservoir fluids. Sample acquisition allows determination of critical information for assessing the economic value of reserves. In addition, optimal production strategies can be designed to handle these complex fluids. In openhole sampling, initially, the flow from the formation contains considerable filtrate, but as this filtrate is drained from the formation, the flow increasingly becomes richer in formation fluid. That is, the sampled flow from the formation contains a higher percentage of formation fluid as pumping continues.

It is well known that fluid being pumped from a wellbore undergoes a cleanup process in which the purity of the sample increases over time as filtrate is gradually removed from the formation and less filtrate appears in the sample. As the composition of the sampled formation fluid changes, so do the optical and physical properties of the sampled fluid, such as optical absorption, fluorescence, refractive index, viscosity, density, sound speed, and bulk modulus. A number of different measurements are used to determine various optical and physical properties of a fluid downhole in real time. Measuring these properties of the fluid therefore provides insight into a sample's purity.

When extracting fluids from a formation, it is desirable to quantify the cleanup progress, that is, the degree contamination from filtrate in real time. If it is known that there is too much filtrate contamination in the sample (more than about 10%), then there is no reason to collect the formation fluid sample in a sample tank until the contamination level drops to an acceptable level. On the other hand, if by pumping for very long time, it is possible to achieve only slightly better contamination level, an operator ends up wasting very expensive rig time and also risks the very costly possibility of allowing a tool to become stuck in the wellbore. Thus, there is a need to determine how long one must pump to obtain a suitable purity sample from the formation.

When pumping first begins, the fluid being pumped contains a large amount of mud filtrate contamination and the fluid filtrate percentage is decreasing at the fastest rate. This process of decreasing fluid filtrate contamination is referred to as sample clean up. Later, the pumped fluid contains less contamination and the fluid filtrate percentage decreases at a slower rate. Oliver Mullins, Jon Schroer, and G. Beck have a published paper on curve fitting of sampled absorbance values versus time data to quantify clean up in real time, "Real Time Determination of Filtrate Contamination During Openhole Wireline Sampling by Optical Spectroscopy," SPWLA, 41$^{st}$ Annual Meeting, Dallas, Tex. June 2000. See also, U.S. Pat. Nos. 6,274,865 and 6,350,986.

In this paper, Mullins et al. assume that the rate of sample cleanup as measured by observing optical density progresses as $t^{-5/12}$ where t is time. This clean up rate is based on empirical experience in the Gulf of Mexico and elsewhere. However, Mullins et al. also state that, for extended pumping durations, they believe that the sample cleanup rate for shallow invasion progresses as $t^{-1/3}$ and that the cleanup rate for deeper invasions progresses as $t^{-2/3}$. Clearly, an assumption of a sample clean rate of $t^{-5/12}$ can be rigid and inapplicable to real time situations. Moreover, using time as a fitting parameter necessarily assumes a constant pumping rate. Another problem with monitoring sample clean up over time by looking at optical absorption over time is that sand particles and other particulates can cause considerable scattering, which causes the absorption values measured over time to "jump" and appear noisy. Thus, there is a need for a more flexible model so that curve-fitting can provide additional usable information regarding formation properties and characteristics for downhole pumping in real time.

SUMMARY OF THE INVENTION

The present invention provides a method of quantifying sample clean up in real time by curve-fitting at least two measurements over time or over volume of the same optical or physical properties of fluid samples taken from a formation surrounding a borehole. Sample fluid is extracted from the formation surrounding the borehole. As fluid continues to be extracted from the formation, the composition of the sampled fluid changes, altering the measured values of an optical or physical property for the sampled fluid. The present invention regresses measurements of the sampled formation fluid properties over time, to fit the preferred functional form to the acquired measured data points. In a preferred embodiment of the invention, iterative methods are provided that enable a user to determine an asymptotic value of a physical property, e.g., absorbance, as well as the percent that the current sample has achieved toward reaching the asymptotic value. The present invention also provides a projected time or volume to reach the asymptotic value. If the projected time or volume required to reach that asymptotic value is determined to be excessive, the operator may abandon extracting fluid from the formation region. In another embodiment of the present invention, a more general method enables the user to estimate, from the value of a fitted parameter, the speed at which cleanup will occur. In another embodiment, the measurements are indicative of formation physical properties such as formation damage.

BRIEF DESCRIPTION OF THE FIGURES

Other objects and advantages of the invention will become apparent upon reading the following detailed description and upon reference to the accompanying drawings in which.

DETAILED DESCRIPTION OF A PREFERRED EMBODIMENT

Figure 1:
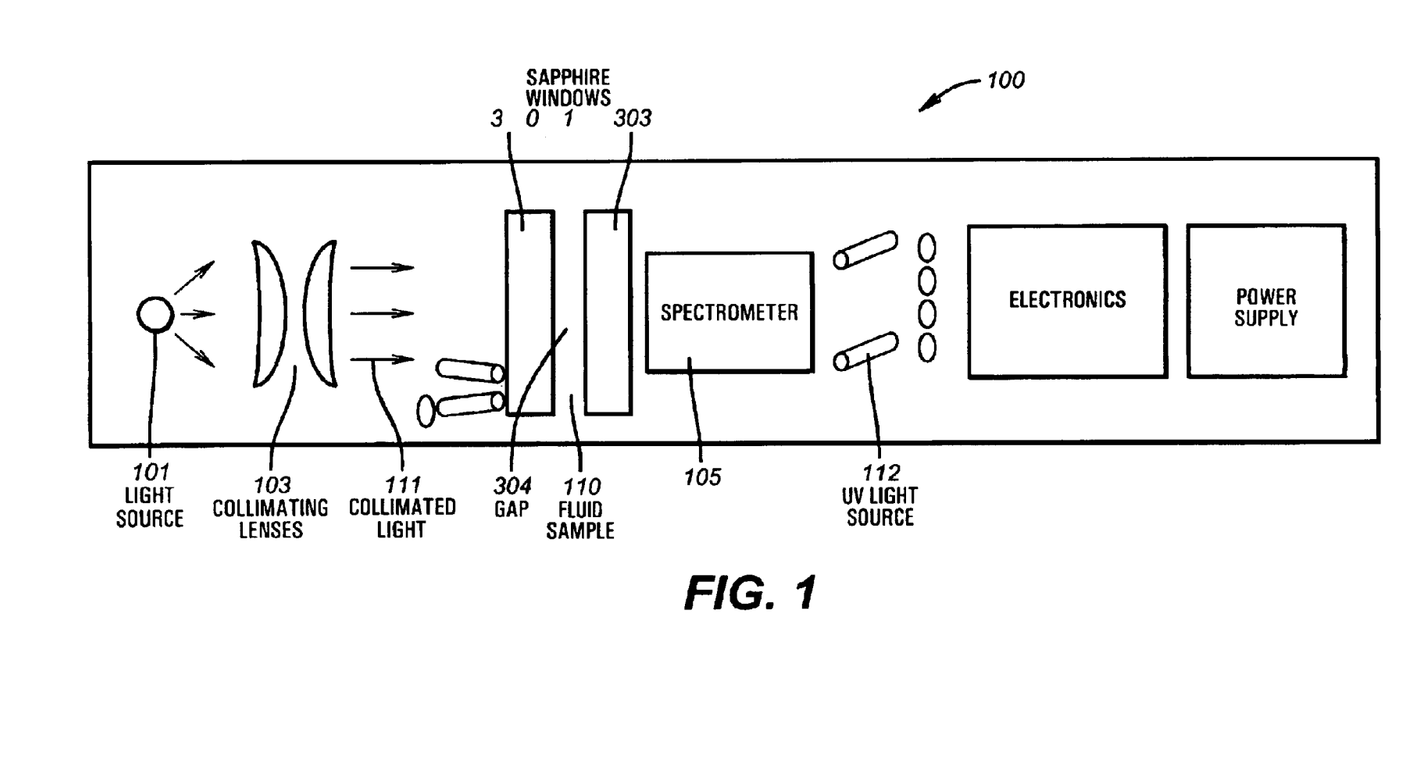
FIG. 1 is a diagram of the Fluid Characterization Module.
Figure 10:
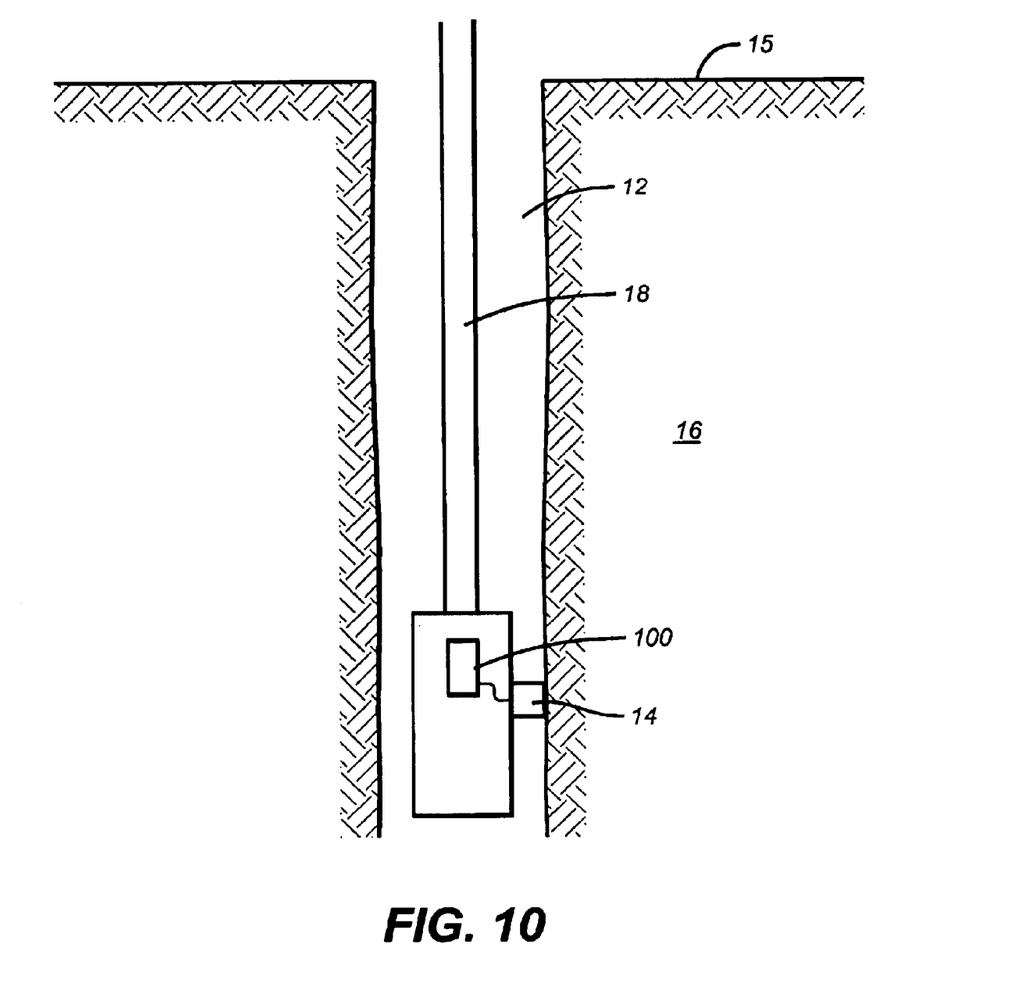
FIG. 10 is an illustration of the present invention deployed from a wireline or drill string in a down hole sampling environment.

FIG. 1 illustrates a schematic representation for a downhole fluid characterization module, as, for example, the Baker Atlas SampleView$^{SM}$ tool. FIG. 10 is an illustration of the present invention 100 deployed form the Earth surface 15 in a borehole 12 from a wireline or drill string 18 sampling 14 a formation 16. In FIG. 1, A light source 101 (e.g. tungsten light bulb) emits light toward a sample 110, and this light is collimated by a collimating lens device 103 lying between the light source and the sample 110. The collimated light 111 is incident generally perpendicular to a first sapphire window 301 adjacent sample 110. Sapphire windows 301 and 303 lie generally perpendicular to the collimated beam of light and are separated by a gap or channel 304 enabling a fluid sample 110 to flow between them. Reflected and fluoresced light can be monitored over time in the spectrometer 105 to determine sample properties. The existing tools (FIG. 1) can be fitted with a UV light source 112, which can be turned on when the tungsten light source 101 is turned off. The same spectrometer, comprising single wavelength filters over photodiodes, enables collecting the crude oil fluorescence.

One of the problems with monitoring the cleanup over time by looking at the optical absorption over time (over a 2 mm pathlength) is that sand particles and other particulates cause considerable scattering, which makes the absorption over time "jump" a lot and look very noisy.

Monitoring cleanup over time by monitoring refractive index (which is an interface-based technique) is less sensitive to particulates in the fluid stream because one is only looking at a thin layer of fluid that is in direct contact (at the interface) with the sapphire window. Similarly, for crude oils, fluorescence only sees a thin layer of crude oil near the window and therefore, it is very insensitive to particulates in the stream.

The present invention does not depend upon an assumption about the rate of cleanup. The present invention assumes that the functional form for the cleanup is best approximated by $\ln(OD)=C-D/t^p$ discussed below. Prior art systems calculated the percentage of contamination by assuming that, upon reaching asymptotic optical absorbance, the sample had achieved zero contamination. The present invention, however, assumes that a dynamic equilibrium can be reached between sample clean up and continued filtrate incursion, depending on the ratio of vertical to horizontal permeability and other factors. Thus, the contamination may not drop to zero, but only to some minimum value, even after very long pumping times. That is, the asymptotic contamination level represents the minimum contamination but, not necessarily, zero contamination.

In general, the physical properties of the pumped sample fluid mixture change measurably over time depending upon the amount of filtrate contamination present in the formation at the sample location. The present invention provides an iterative procedure to determine the asymptotic value to produce the best fit to the preferred curve fitting. The present invention calculates current sample contamination level as a percentage of the ultimately-achievable sample contamination (asymptotic) level. This calculation does not assume that the ultimately achievable contamination is zero. By fitting a curve for this calculation to the change in one of the measured properties over time, the present invention calculates, in real time, the current contamination level as a percentage of the ultimately achievable (asymptotic) cleanup contamination level. The present invention also calculates the amount of time for which pumping should continue in order to reach any desired percentage of the asymptotic limit.

In a preferred embodiment, the present invention fits the optical density to a form of $$OD=\exp\{mt^{-p}+b\} \quad (1)$$

where p is a negative number, OD is the optical density and b is an asymptotic value for a physical property. Equation 1 is functionally equivalent to the form $$\ln(OD)=C-D/t^p, \quad (2)$$

where C=b and m=−D and p is a positive number due top appearing in the denominator.

As an example of formation clean-up, simulation results and actual field data for optical density can be fitted to forms such as, $Y=mX^{-p}+b$ or $\ln(Y)=mX^{-p}+b$. Using the sample contamination concentration as Y and the pumping time as X, simulation results fit these forms well, especially the logarithmic form. Because the optical density (OD) is an indicator of clean-up, the OD data can be used as Y and the pumping time can be used as X. If the pumping speed changes many times during the course of clean-up, the cumulative volume pumped is used as X instead of time.

A small p value indicates that clean-up process is slow and it will take longer to obtain a quality sample, while a high value of p indicates that the clean-up process will be faster and the chance for obtaining a sample of the desired purity is high. The value of b is used as an indicator for clean-up to the best sample quality achievable (the asymptotic value). By comparing the current OD value with the b value, the current sample contamination percentage is obtained. The future sample quality is estimated using the fitted values of m, p, and b, and a decision can be made as to whether to continue or to stop the pumping process if the estimated future sample quality is not good enough.

Figure 2:
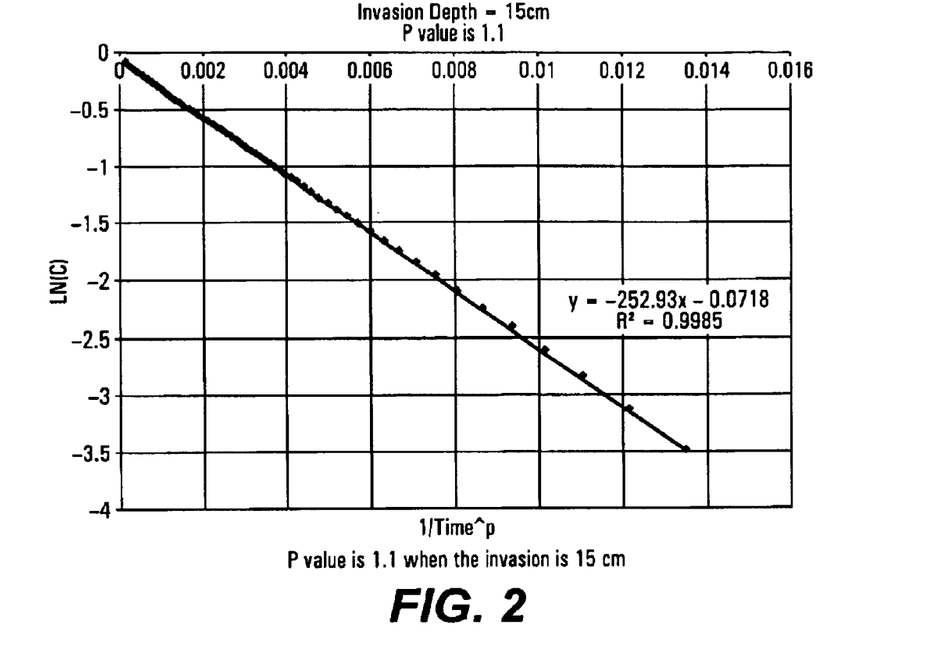
FIG. 2 is a graph of a function of sample contamination concentration against a time function at an invasion depth of 15 cm.
Figure 3:
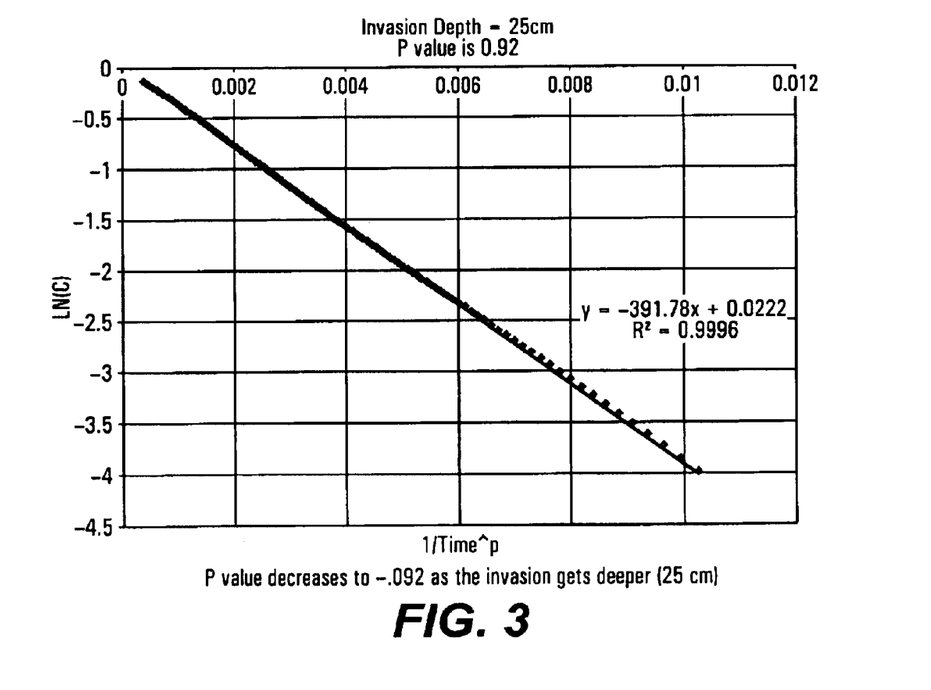
FIG. 3 is a graph of a function of sample contamination concentration against a time function at an invasion depth of 25 cm.

The power of X, which is -p, (where p is a positive number) can be used as an indicator for the progress of the clean-up process. FIG. 2 is a graph 200 of ln(c) vs. $1/t^p$ for a nominal filtrate invasion depth of 6 inches (15 cm) or less. At this invasion depth, the value of p is in the range of 1.0–1.1, as shown in FIG. 2. FIG. 3 is a graph 300 of ln(c) versus $1/t^p$. As the invasion depth increases, the p value decreases below 1.0 and can be closer to 0.5 (FIG. 3). Consequently, when the p value is small, and the calculated current contamination is high, there will be little chance of obtaining a high quality sample and it will take a long time, perhaps too long to obtain the desired sample purity.

Figure 5:
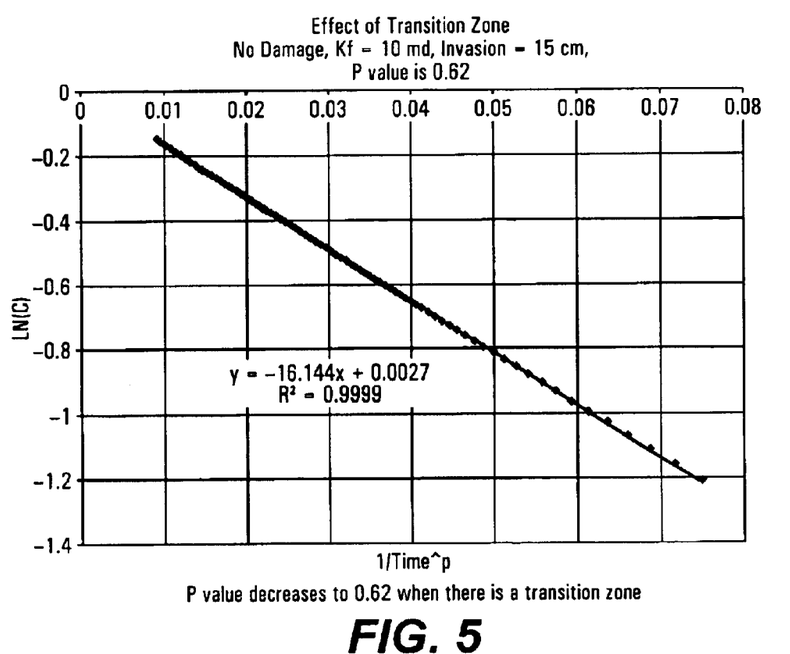
FIG. 5 is a graph of a function of sample contamination concentration against a time function with a transition zone of 15 cm.

FIG. 5 is a graph 500 of lu(c) versus $1/t^p$ for no damage and invasion=15 cm. When the invasion profile is gradual, meaning a transition zone is present instead of sharp invasion boundary, the value of p decreases below 1.0 as shown in FIG. 5. The value of p depends on the thickness of the transition zone between the region of filtrate and region of formation fluid. The thicker the transition zone, the lower the p value. This gradual transition has a similar effect to that of deep invasion. When the invasion is deep, then the clean fluid from the fresh zone will be mixed with the filtrate while it flows toward the probe. Hence a deep invasion will have a thick transition zone, and clean-up for that zone will take a long time. In FIG. 5, the value of p is 0.62 indicating a longer time necessary for cleanup.

Figure 4:
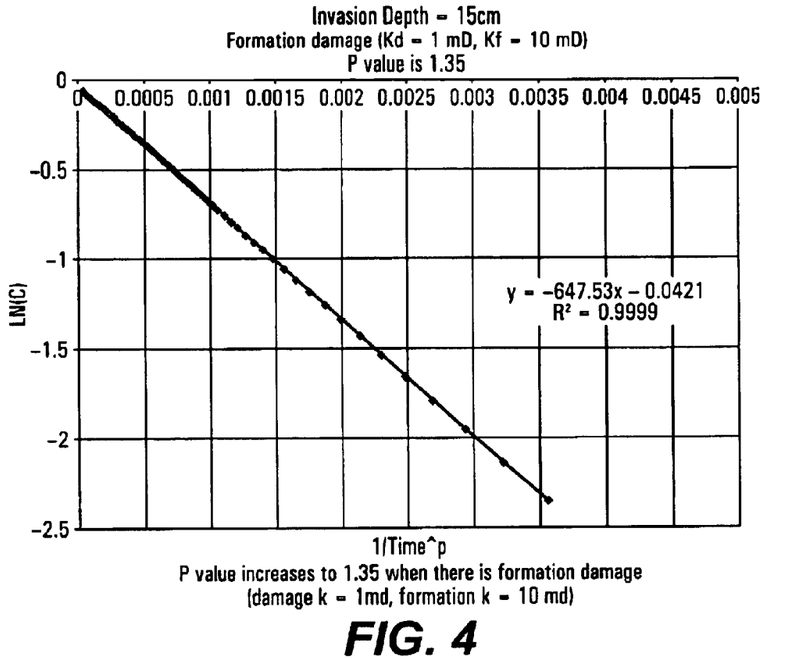
FIG. 4 is a graph of a function of sample contamination concentration against a time function at an invasion depth of 15 cm and with formation damage.
Figure 6:
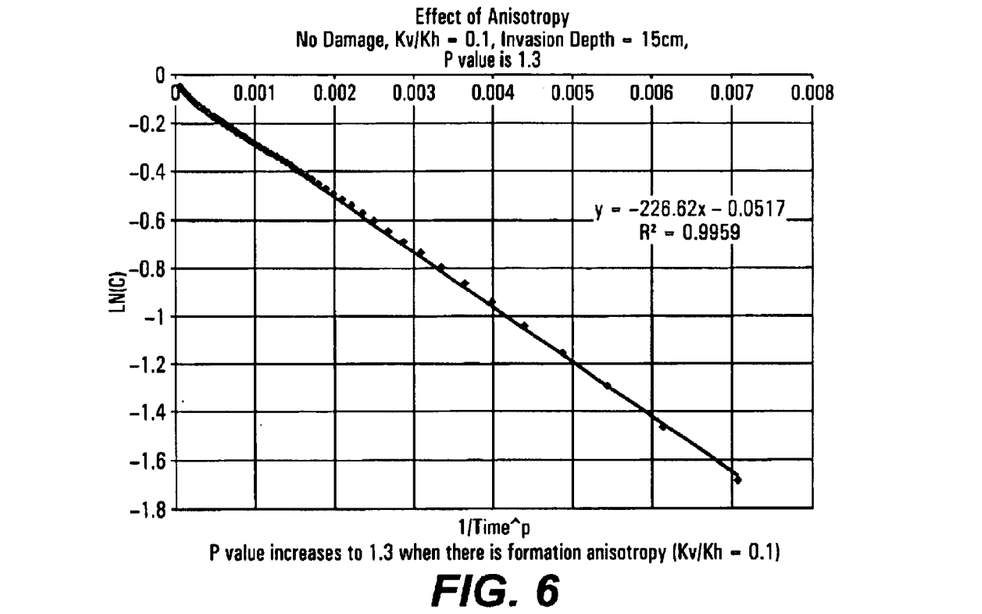
FIG. 6 is a graph of a function of sample contamination concentration against a time function at an invasion depth of 15 cm and with an anisotropic formation.
Figure 7:
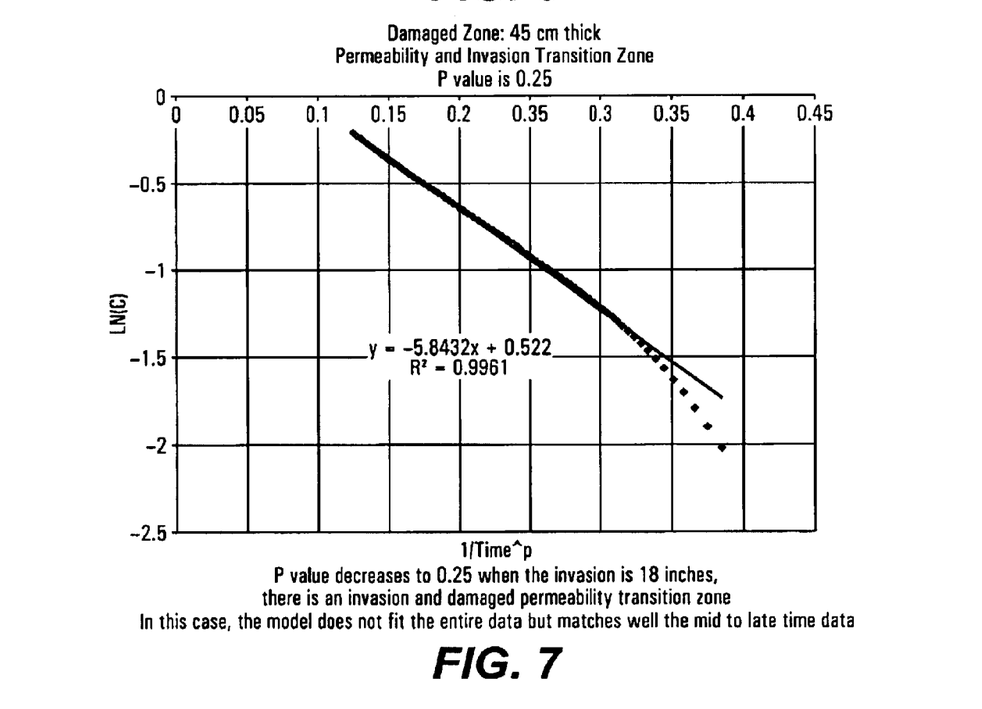
FIG. 7 is a graph of a function of sample contamination concentration against a time function at an invasion depth of 45 cm with a damaged permeability zone.

Formation damage can also affect the clean-up process. The clean-up can be improved when the formation near the wellbore is damaged or when the near wellbore formation permeability is less than the true formation permeability due to the small particle invasion. FIG. 4 is a graph 400 ln(c) vs. $1/t^p$ for an invasion depth of 15 cm. As an example, FIG. 4 indicates formation damage with permeability in the damaged region $k_d$=1mD and permeability in the formation $k_f$=10mD, and an invasion depth of 15 cm. The value of p increases to p=1.35. Anisotropy in the formation also quickens the clean-up process. FIG. 6 is a graph 600 of ln(c) vs. $1/t^p$. In FIG. 6, with no formation damage and a ratio of vertical to horizontal permeability of $K_v/K_h$=0.1 and an invasion depth of 15 cm, there is a p-value of 1.3, indicating a quick clean-up. FIG. 7 is a graph 700 of ln(c) vs. $1/t^p$. FIG. 7 illustrates a graph 700 of the data for a damaged zone, with permeability and invasion transition zone of 45 cm. The value of p is 0.25 indicating a long cleanup process. In this case, the model does not fit the entire data but does match the middle to latter time data.

Figure 8:
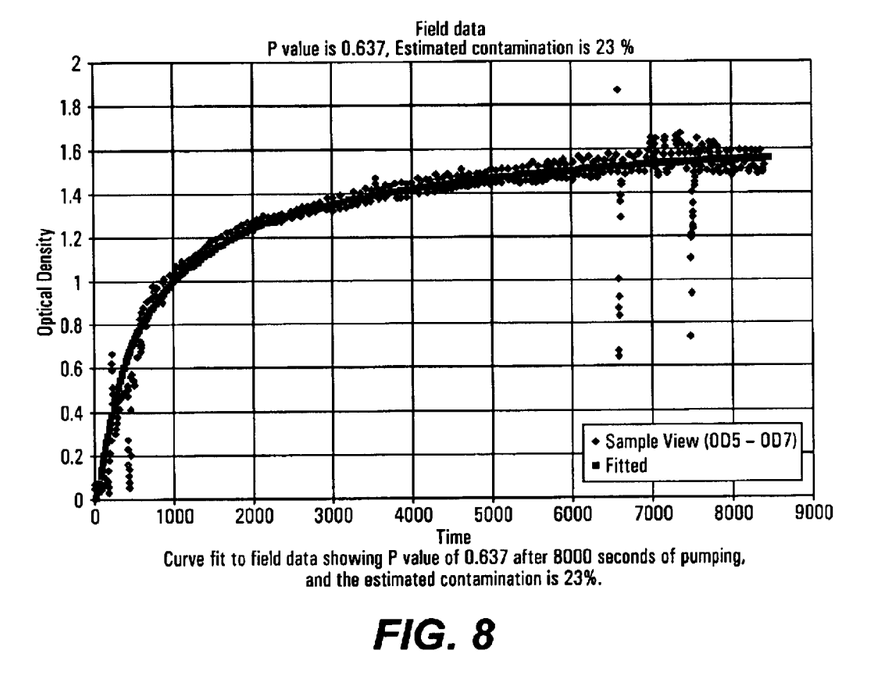
FIG. 8 is a graph of a curve fitted to field data after 8000 seconds of pumping.

FIG. 8 illustrates a curve 800 fit to a field data shown a p value of 0.637 after 8000 seconds of pumping and the estimated contamination is 23%. FIGS. 9A through 9D show steps for performing the invention.

Figure 9A:
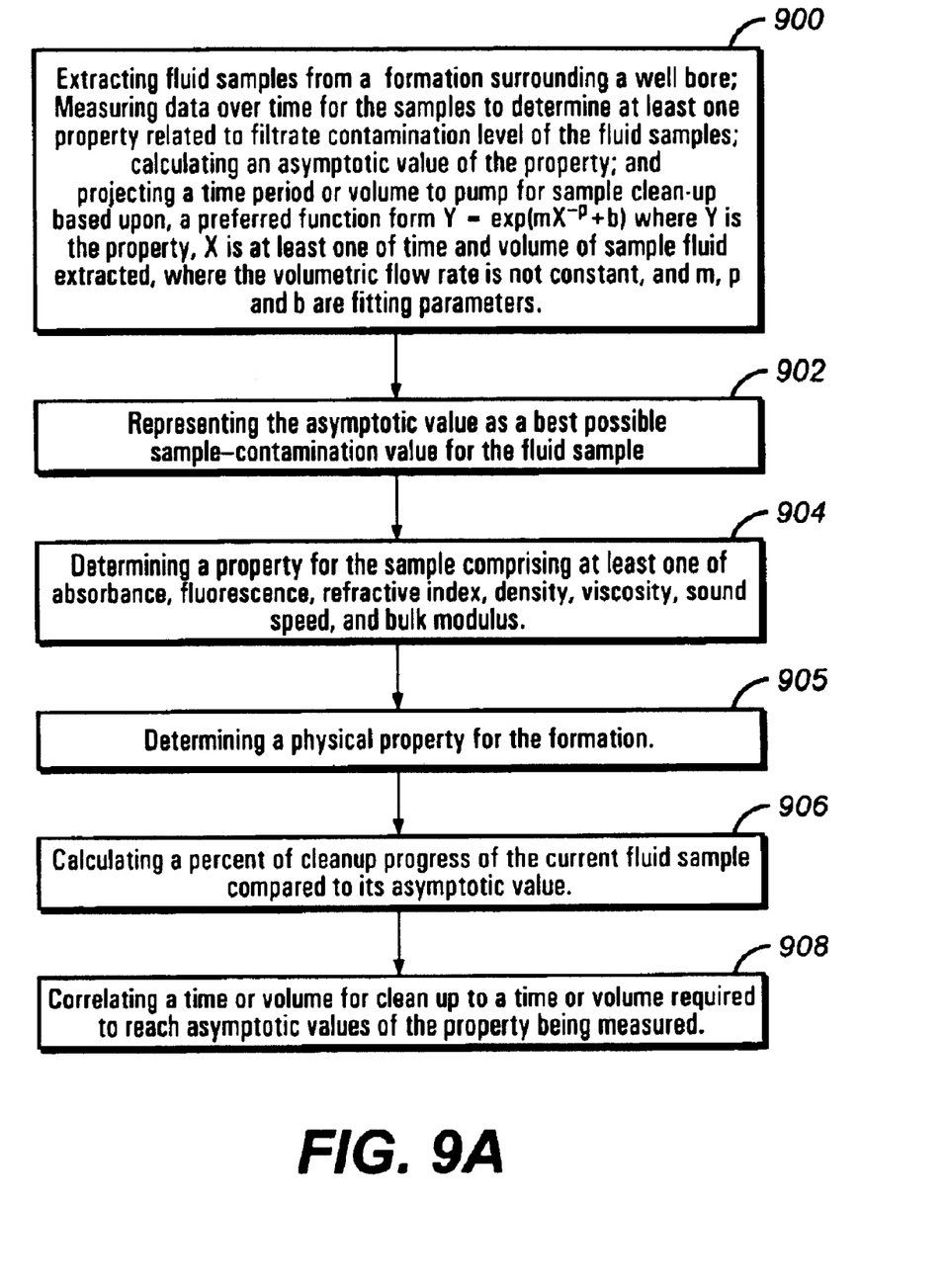
FIGS. 9A–9D are flow charts showing one example of the steps of carrying out the present invention.

Turning now to FIG. 9A, graph 900 extracting fluid samples from a formation surrounding a well bore; measuring data over time for the samples to determine at least one property related to filtrate contamination level of the fluid samples; calculating an asymptotic value of the property; and projecting a time period or volume to pump for sample clean-up based upon, a preferred functional form Y=exp(mX$^{-p}$+b) where Y is the property, X is at least one of time and the volume of sample fluid extracted, where the volumetric flow rate is not constant, and m, p, and b are fitting parameters. 902 representing the asymptotic value as a best possible sample-contamination value for the fluid sample. 904 determining a property for the sample comprising at least one of absorbance, fluorescence, refractive index, density, viscosity, sound speed, and bulk modulus. 906 calculating a percent of cleanup progress of the current fluid sample compared to its asymptotic value. 908 correlating a time or volume for clean up to a time or volume required to reach asymptotic values of the property being measured.

Figure 9B:
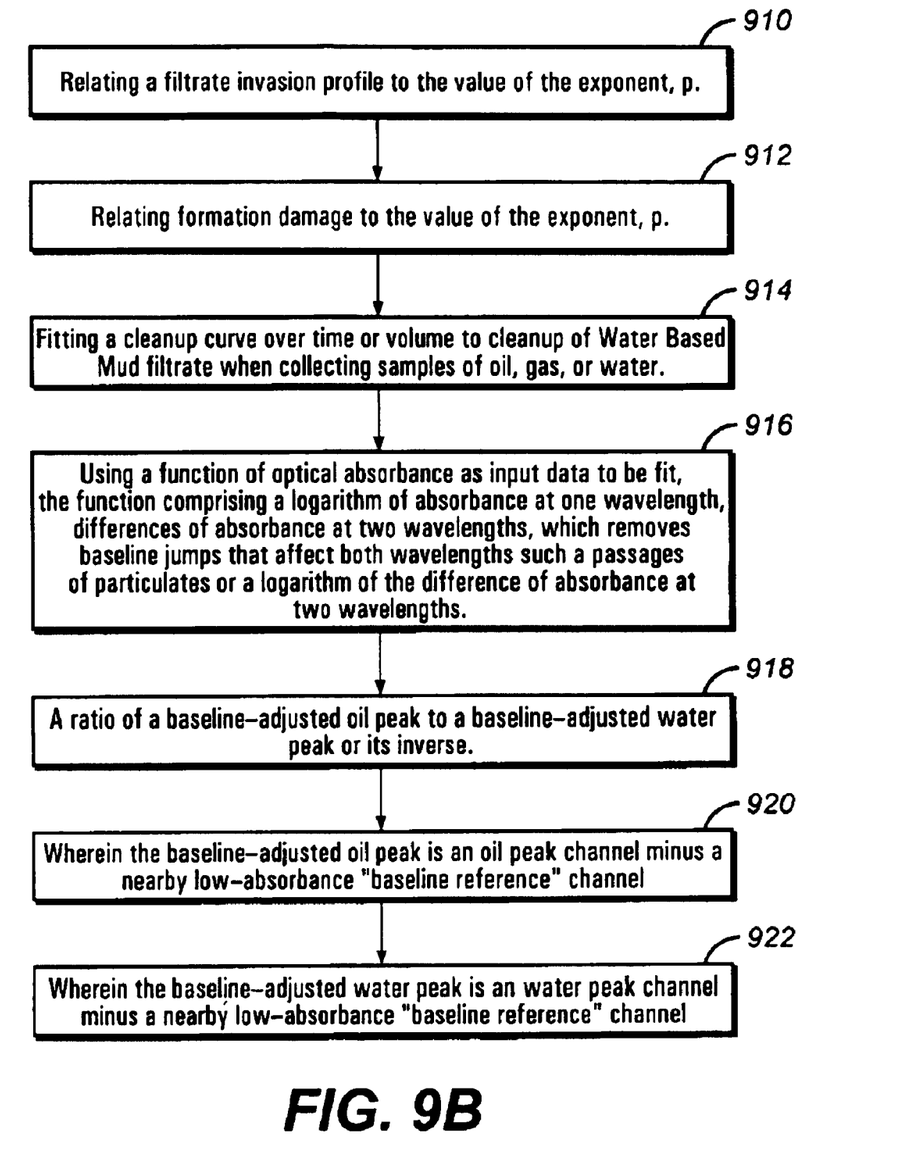

Turning now to FIG. 9B, 910 relating a the filtrate invasion profile to the value of the exponent, p. 912 relating formation damage to the value of the exponent, p. 914 fitting a cleanup curve over time or volume to cleanup of Water Based Mud filtrate when collecting samples of oil, gas, or water. 916 using a function of optical absorbance as input data to be fit, the function comprising a logarithm of absorbance at one wavelength, differences of absorbance at two wavelengths, which removes baseline jumps that affect both wavelengths such as passages of particulates or a logarithm of the difference of absorbance at two wavelengths. 918 a ratio of a baseline-adjusted oil peak to a baseline-adjusted water peak or its inverse. 920 wherein the baseline-adjusted oil peak is an oil peak channel minus a nearby low-absorbance "baseline reference" channel. 922 wherein the baseline-adjusted water peak is a water peak channel minus a nearby low-absorbance "baseline reference" channel.

Figure 9C:
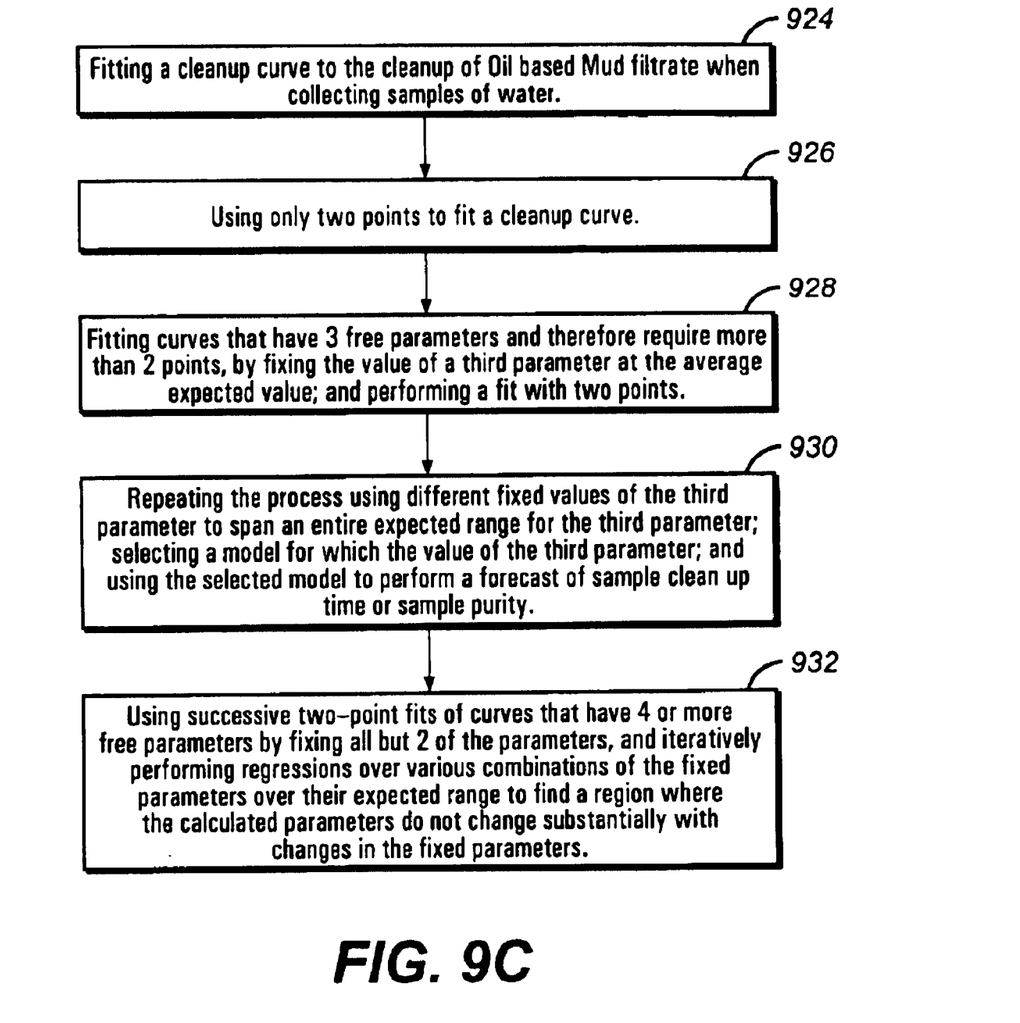

Turning now to FIG. 9C, 924 fitting a cleanup curve to cleanup of Oil Based Mud filtrate when collecting samples of water. 926 using only two points to fit a cleanup curve. 928 fitting curves that have 3 free parameters and therefore require more than 2 points, by fixing the value of a third parameter at the average expected value; and performing a fit with two points. 930 repeating the process using different fixed values of the third parameter to span an entire expected range for the third parameter; selecting a model for which values of the calculated parameters show least change with an assumed value of the third parameter; and using the selected model to perform a forecast of sample clean up time or sample purity. 932 using successive two-point fits of curves that have 4 or more free parameters by fixing all but 2 of the parameters, and iteratively performing regressions over various combinations of the fixed parameters over their expected range to find a region where calculated parameters do not change substantially with changes in the fixed parameters.

Figure 9D:
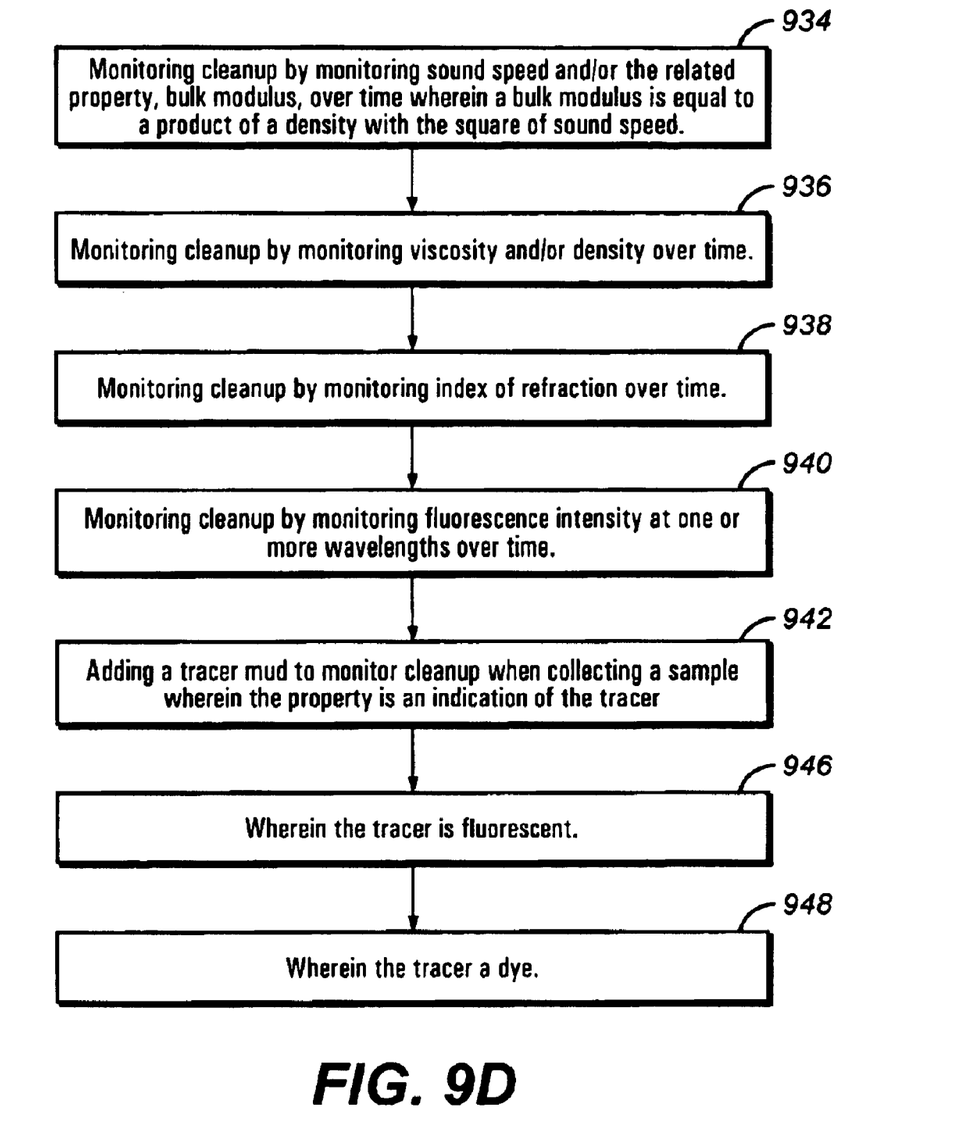

Turning now to FIG. 9D, 934 monitoring cleanup by monitoring sound speed and/or the related property, bulk modulus, over time wherein a bulk modulus is equal to a product of a density with the square of sound speed. 936 monitoring cleanup by monitoring viscosity and/or density over time. 938 monitoring cleanup by monitoring index of refraction over time. 940 monitoring cleanup by monitoring fluorescence intensity at one or more wavelengths over time. 942 adding a tracer mud to monitor cleanup when collecting a sample wherein the property is an indication of the tracer. 946 wherein the tracer is fluorescent. 948 wherein the tracer is a dye.

The functional form that is a best fit to simulation data regardless of invasion depth or formation damage is OD=exp(mt$^{-p}$+b), so that at longer times, the OD stops changing because the time-dependent term goes to zero as time goes to infinity. That form is equivalent to the form, $\ln(OD) = C - D/t^p$ where $C = b$, $m = -D$, and $p$ is a positive number. Curve fitting of sample clean-up using the form of $$\ln(Y) = mX^{-p} + B$$

where Y=optical or physical properties such as absorbance or fluorescence at some wavelength as the sample as it cleans up, X=Time since started pumping sample or, more correctly, the cumulative volume pumped, when the volumetric flow rate is not constant.

Applying the functional form $\ln(OD) = A*1/\text{Time}^n + B$ to simulation results, shows that: a) In a simple system with no permeability damage and a sharply-defined filtration zone (100% filtrate zone followed by 0% zone), the n value is 1.1; b) Adding permeability damage to system, speeds up the cleaning process, and the n value is 1.3; c) Using a gradual filtrate contamination, in which contamination decreases as moving away from wellbore (that is 100, 80, 60 . . . and 0%) then the n value is 0.75; d) Adding damage to the system (c), then the n value is 1.0; and e) Adding a permeability change due to formation damage, then the n value can vary from 0.25 to 0.5. Fitting formation clean-up simulation results and some field data (optical density) to the above functional form, the following findings are provided.

Using the sample contamination concentration as Y and the cumulative pump-volume as X, simulation results fit the form very well. Because the optical density (OD) is an indicator of clean-up, the OD data can be used as Y and pump-time can be used as X. If the pumping speed changes many times during the course of clean-up, the cumulative volume pumped should be used as X instead of time. The power X, which is $-p$ (where p is a positive number), can be used as an indicator for the clean-up process. For a nominal invasion of 6 inches or less, p is near 1.0–1.1.

As the invasion gets deeper, p decreases below 1.0 and becomes closer to 0.5. In a deep invasion of 20 inches, p drops to 0.25. When the invasion profile is gradual, this indicates that there is a transition zone instead of a sharp invasion boundary, and p decreases below 1.0. The p value will depend on the thickness of the transition zone, the thicker the zone, the lower the p value. A similar effect is found for deep invasion. When the invasion is deep, then the clean fluid from the fresh zone will be mixed with the filtrate while it flows toward the probe. Hence the deep invasion will have a thick transition zone, and it will take a longer time to clean-up that zone.

When the formation near the wellbore is damaged, that is the near wellbore formation permeability is less than the true formation permeability due to the small particle invasion, the clean-up can be improved as discussed in papers in the Society for Petroleum Engineers, papers SPE 39817 and SPE 48958. The formation anisotropy also helps the clean-up process (see SPE papers, SPE 39817 and SPE 48958). When there is a damage or a formation anisotropy, the p value increases above 1.0–1.1 up to 1.3–1.4. Hence a small p value indicates that the clean-up process will be slow and will take longer to get a quality sample of the desired purity.

A high p value indicates that the clean-up process will occur quickly and the chance for a good quality sample is high. The B value can be used as the best sample quality achieved. By taking the ratio of the current OD value to the B value, the fraction of the cleanest possible sample is obtained. Using the fitted values of m, p, and B, the future sample quality can be estimated and a decision as to whether to continue or stop the sample pumping process can be made. When the p value is small, and the calculated current contamination is high, there will be little chance of obtaining a high quality sample of the desired purity and it will take an infeasible amount of time to obtain the desired sample.

It is primarily the aromatic and polynuclear aromatics molecules that fluoresce. That is why, crude oil usually fluoresces much more than does the filtrate of oil based mud (OBM). For environmental reasons, synthetic OBMs are designed to be as aromatic free as possible but they may pick up some aromatic contamination from drilling or they may have small amounts of aromatic emulsifiers or fluid loss control materials added to them. Also, the filtrate of water-based mud has little or no fluorescence because water itself is non-fluorescing. Some compounds that dissolve in water may fluoresce. Furthermore, one could deliberately add fluorescent compounds to water based or oil based mud as fluorescent tracers.

The present invention can plot a measured property, P, over time, t, and try to forecast the value of P at some future time by fitting a curve, f(t), to the measured data. The forecast is then just an extrapolation of the curve that was fit to the measured data. That is, we can fit our measurements by a curve, $$P = f(t) \tag{3}$$

As long as there are only two free parameters in the function, f(t), to be fit, we need only two points of this curve. As a specific example, suppose that the functional form given by, $$P = a + bt^m \tag{4}$$

For any fixed power of m, the present invention can determine the coefficients, a and b, from the two points, $(t_1, P_1)$ and $(t_2, P_2)$, by solving the pair of simultaneous equations (5) and (6).

$$P_1 = a + bt_1^m \tag{5}$$

$$P_2 = a + bt_2^m \tag{6}$$

Solving simultaneous Equations 5 and 6 for a and for b, the invention obtains, $$a = (P_1 t_2^m - P_2 t_1^m)/(t_2^m - t_1^m) \tag{7}$$

$$b = (P_2 - P_1)/(t_2^m - t_1^m) \tag{8}$$

To reduce the effects of errors in the measurements of the two points, $(t_1, P_1)$ and $(t_2, P_2)$ on the calculated values of fitting parameters, a and b, we can average a cluster of points in the neighborhood of $(t_1, Pt_1)$ to create an average neighborhood value, $(<t_1>, <P_1>)$ for the region of the first point. Similarly, we can average a cluster of points in the neighborhood of $(t_2, P_2)$ to create an average neighborhood value, $(<t_2>, <P_2>)$. Finally, we can substitute the average values for the two neighborhoods around these points into Equations 7 and 8.

It is advisable not to choose a pair of points (or averages of points), which are too close to one another in time because such a choice would increase the uncertainty in the fitting parameters, a and b, for any given uncertainty in the values of the points (or point averages) used to calculate them. Of course, one has to balance the tradeoff between picking points that are as far apart from one another in time as possible and including a noisy point, such as those that are common at very early times. That balance can be achieved through a combination of experience and some real-time trial and error in picking point pairs for which the fitting parameters do not change substantially with the choice of point pairs used to calculate them.

For a function, f(t), that has 3 free parameters and therefore requires more than 2 points, we can fix the value of the third parameter (e.g., the power of time in Equation 5) at the average expected value and then proceed to perform the fit with two points as before. We can then repeat this process over and over again, using different fixed values of this third parameter to span its entire expected range. Then, we can select that model for which the values of the 5 calculated parameters show the least change with the assumed value of the third parameter. We can use the selected model to perform the forecast.

Generalizing this process, the present invention uses successive two-point fits of curves that have four or more free parameters by fixing all but two of the parameters, and iteratively performing regressions over various combinations of the fixed parameters over their expected ranges to find a region where the calculated parameters do not change much with changes in the fixed parameters.

In the specific case where the property being fit is a function of the optical absorption, we can select certain particularly useful functions of the absorption. One such function is the ratio of a baseline-adjusted oil peak to a baseline-adjusted water peak or its inverse. This function is particularly useful in monitoring the cleanup from water based mud filtrate to native crude oil. Its inverse is particularly useful in monitoring the cleanup from oil based much filtrate to connate water, when it is desired to collect a sample of water.

The baseline-adjusted oil peak is an oil peak channel (near 1740 nm) minus a nearby low-absorbance "baseline reference" channel (e.g. channels at 1300 or 1600 nm). The baseline-adjusted water peak is a water peak channel (near 1420 or 1935 nm) minus a nearby low-absorbance "baseline reference" channel (e.g. channels at 1300 or 1600 nm). Substituting time equals infinity into our forecasting model lets us estimate the limiting value of property, P, at infinite time. Dividing our current value of property, P, by its forecasted infinite time value gives us the fraction of the way that we are to the infinite time value, which is indicative of cleanup progress.

The present invention may also be utilized by adding a water soluble fluorescent tracer or a dye to water based mud to monitor cleanup when collecting a connate water sample or an oil soluble fluorescent tracer or dye to oil based mud when collecting an oil sample. This enables the present invention to distinguish between the connate water and the filtrate based on the fluorescent or dye tracer or tag, which could have a very different color of fluorescence or dye than the native fluids.

The present invention has been described as method and apparatus operating in a down hole environment in the preferred embodiment, however, the present invention may also be embodied as a set of instructions on a computer readable medium, comprising ROM, RAM, CD ROM, Flash or any other computer readable medium, now known or unknown that when executed cause a computer to implement the method of the present invention. While a preferred embodiment of the invention has been shown by the above invention, it is for purposes of example only and not intended to limit the scope of the invention, which is defined by the following claims.

What is claimed is:

1. A method for quantifying the progress of sample cleanup in real time in a wellbore environment, comprising:

extracting fluid samples from a formation surrounding a well bore;

measuring data over time for the samples to determine at least one property related to filtrate contamination level of the fluid samples;

calculating an asymptotic value of the property; and projecting a time period or volume to pump for sample clean-up based upon, a preferred functional form $Y=\exp(mX^{-p}+b)$ where Y is the property, X is at least one of time and the volume of sample fluid extracted, where the volumetric flow rate is not constant, and m, p, and b are fitting parameters.

2. The method of claim 1, further comprising:

representing the asymptotic value as a best possible sample-contamination value for the fluid sample.

3. The method of claim 1, further comprising:

calculating the asymptotic value by fitting a curve to the measured data through an iterative procedure.

4. The method of claim 1, further comprising:

determining a property for the sample comprising at least one of absorbance, fluorescence, refractive index, density, viscosity, sound speed, and bulk modulus.

5. The method of claim 1, further comprising:

determining a physical property for the formation.

6. The method of claim 1, further comprising:

calculating a percent of cleanup progress of the current fluid sample compared to its asymptotic value.

7. The method of claim 1, further comprising:

correlating a time or volume for clean up to a time or volume required to reach asymptotic values of the property being measured.

8. The method of claim 1, further comprising:

relating a the filtrate invasion profile to the value of the exponent, p.

9. The method of claim 1, further comprising:

relating formation damage to the value of the exponent, p.

10. The method of claim 1, further comprising:

fitting a cleanup curve over time or volume to cleanup of Water Based Mud filtrate when collecting samples of oil, gas, or water.

11. The method of claim 10, further comprising:

using a function of optical absorbance as input data to be fit, the function comprising a logarithm of absorbance at one wavelength, differences of absorbance at two wavelengths, which removes baseline jumps that affect both wavelengths such as passages of particulates or a logarithm of the difference of absorbance at two wavelengths.

12. The method of claim 11, wherein the function comprises:

a ratio of a baseline-adjusted oil peak to a baseline-adjusted water peak or its inverse.

13. The method of claim 12, wherein the baseline-adjusted oil peak is an oil peak channel minus a nearby low-absorbance "baseline reference" channel.

14. The method of claim 12, wherein the baseline-adjusted water peak is a water peak channel minus a nearby low-absorbance "baseline reference" channel.

15. The method of claim 1, further comprising:

fitting a cleanup curve to cleanup of Oil Based Mud filtrate when collecting samples of water.

16. The method of claim 1, further comprising:

using only two points to fit a cleanup curve.

17. The method of claim 1, further comprising:

fitting curves that have 3 free parameters and therefore require more than 2 points, by fixing the value of a third parameter at the average expected value; and performing a fit with two points.

18. The method of claim 17, further comprising:

repeating the process of claim 17, using different fixed values of the third parameter to span an entire expected range for the third parameter;

selecting a model for which values of the calculated parameters show least change with an assumed value of the third parameter; and using the selected model to perform a forecast of sample clean up time or sample purity.

19. The method of claim 17, further comprising:

using successive two-point fits of curves that have 4 or more free parameters by fixing all but 2 of the parameters, and iteratively performing regressions over various combinations of the fixed parameters over their expected range to find a region where calculated parameters do not change substantially with changes in the fixed parameters.

20. The method of claim 1, further comprising:

monitoring cleanup by monitoring sound speed and/or the related property, bulk modulus, over time wherein a bulk modulus is equal to a product of a density with the square of sound speed.

21. The method of claim 1, further comprising:

monitoring cleanup by monitoring sample viscosity and/or density over time.

22. The method of claim 1, further comprising:

monitoring cleanup by monitoring index of refraction over time.

23. The method of claim 1, further comprising:

monitoring cleanup by monitoring fluorescence intensity at one or more wavelengths over time.

24. The method of claim 1, further comprising:

adding a tracer mud to monitor cleanup when collecting a sample, wherein the property is an indication of the tracer.

25. The method of claim 24, wherein the tracer is fluorescent.

26. The method of claim 24, wherein the tracer is a dye.

27. An apparatus for quantifying the progress of sample cleanup in real time in a wellbore environment, comprising:

a fluid sample path for samples from a formation surrounding a well bore;

a spectrometer measuring data over time for the samples to determine at least one property related to filtrate contamination level of the fluid samples;

calculating an asymptotic value of the property; and electronics for projecting a time period or volume to pump for sample clean-up based upon, a preferred functional form $Y=\exp(mX_{-p}+b)$ where $Y$ is the property, $X$ is at least one of time and the volume of sample fluid extracted, where the volumetric flow rate is not constant, and m, p, and b are fitting parameters.

28. A computer readable medium containing instructions that when executed by a computer perform a method for quantifying the progress of sample cleanup in real time in a wellbore environment, comprising:

extracting fluid samples from a formation surrounding a well bore;

measuring data over time for the samples to determine at least one property related to filtrate contamination level of the fluid samples;

calculating an asymptotic value of the property; and projecting a time period or volume to pump for sample clean-up based upon, a preferred functional form $Y=\exp(mX^{-p}+b)$ where $Y$ is the property, $X$ is at least one of time and the volume of sample fluid extracted, where the volumetric flow rate is not constant, and m, p, and b are fitting parameters.

* * * * *